(12) United States Patent
Lee et al.

(10) Patent No.: US 6,653,628 B2
(45) Date of Patent: Nov. 25, 2003

(54) ELECTRON SPECTROSCOPIC ANALYZER USING X-RAYS

(75) Inventors: Jae-cheol Lee, Kyungki-do (KR); Yury N. Yuryev, Kyungki-do (KR); Chang-bin Lim, Seoul (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 60 days.

(21) Appl. No.: 09/960,963

(22) Filed: Sep. 25, 2001

(65) Prior Publication Data

US 2002/0040970 A1 Apr. 11, 2002

(30) Foreign Application Priority Data

Sep. 25, 2000 (KR) ............................. 00-56152

(51) Int. Cl.[7] .......................... H01J 40/00; H01J 47/00; A61B 6/00; G01N 23/00; G21K 1/12
(52) U.S. Cl. ........................... 250/305; 378/15
(58) Field of Search ................. 250/305, 306, 250/307; 378/15

(56) References Cited

U.S. PATENT DOCUMENTS 3,822,382 A * 7/1974 Koike ........................ 250/305
4,857,730 A   8/1989 Pierre ........................ 250/305
5,444,242 A * 8/1995 Larson et al. ............... 250/305
6,326,617 B1 * 12/2001 Tomie et al. ............... 250/305

OTHER PUBLICATIONS

"X–ray Photoelectron Spectroscopy (XPS, ESCA)", htt://www.chem.vt.edu/chem–ed/spec/material.xps.html, p. 1, Sep. 18, 2001.
"Electron Spectroscopy", htt://www.chem.vt.edu/chem–ed/spec/material.xps.html, p. 1, Sep. 18, 2001.
X–ray Photoelectron Spectroscopy (XPS), htt://www.mesaplus.utwente.nl/labs/cmal/xps.html, pp 1–2, Sep. 18, 2001.
"5.3 Photoelectron Spectroscopy", http://www.chem.qmt.ac.uk/surfaces/scc/scat5_3.html, pp 1–8, Sep. 18, 2001.
"High Resolution X–ray Photo Electron Spectroscopy", http://www.dl.ac.uk/ASD/RUSTI/xps.html, p. 1, Sep. 18, 2001.
"XPS–Xray Photoelectron Spectroscopy–Novis", http://www.lasurface.com/w_xps/Ag_xps_novis.htm, pp 1–3, Sep. 18, 2001.
"XPS–Xray Photoelectron Spectroscopy–Beginner", http://www.lasurface.com/w_xps/Ag_xps_novis.htm, pp 1–3, Sep. 18, 2001.
"Instruments for Electron Spectroscopy and Surface Analytics", http://www.focus–gmbh.com/APPICATIONS/micros–XPS%20IEF.htm, pp 1–4, Sep. 18, 2001.

* cited by examiner

Primary Examiner—Stephen D. Meier
Assistant Examiner—Alfred E Dudding
(74) Attorney, Agent, or Firm—Burns, Doane, Swecker & Mathis, LLP

(57) ABSTRACT

An electron spectroscopic analyzer using X-rays is provided. The electron spectroscopic analyzer includes an X-ray generator for generating X-rays, an optical system for detecting charged particles emitted from an object irradiated with the X-rays to analyze the object, a vacuum system whose inside is maintained at a low pressure near to vacuum pressure, the vacuum system being provided between the X-ray generator and the optical system, and a blocking unit provided between the X-ray generator and the optical system for preventing elements other than the X-rays emitted from the X-ray generator from flowing into the optical system.

19 Claims, 7 Drawing Sheets

ELECTRON SPECTROSCOPIC ANALYZER USING X-RAYS

This application claims priority under 35 U.S.C. §§ 119 and/or 365 to 00-56152 filed in Republic of Korea on Sep. 25, 2000; the entire content of which is hereby incorporated by reference.

BACKGROUND OF THE INVENTION

1. Field of the Invention

The present invention relates to an electron spectroscopic analyzer using X-rays and, more particularly, to an electron spectroscopic analyzer capable of increasing X-ray transmission efficiency and a signal to noise (S/N) ratio.

2. Description of the Related Art

Electron spectroscopic analyzers using X-rays have a variety of industrial applications. For instance, they are used for obtaining information about the atomic structures and arrays of electrons in atoms of industrially used materials such as semiconductor materials, catalysts and amorphous materials.

Currently used electron spectroscopic analyzers using X-rays are composed of an X-ray generator and an optical system which detects photo electrons emitted from an object onto which X-rays are radiated to analyze the object. However, in these electron spectroscopic analyzers using X-rays, since the optical system (in which the object to be irradiated with X-rays is positioned) is exposed to the air, X-rays generated by the X-ray generator are absorbed by particles in the air while traveling to the object. Particularly for soft X-rays, the absorption ratio of these particles in air is high, which makes the analysis of the intended object practically impossible.

A ratio at which soft X-rays are absorbed into particles in the air can be reduced by connecting an X-ray generator to an optical system using a vacuum system whose inside is maintained at a low pressure near to vacuum pressure. Here, X-rays are generated by bombarding an X-ray generative sample in the X-ray generator with accelerated electrons. However, during the generation of X-rays, electrons are emitted from the X-ray generator and incident on the optical system in addition to the photoelectrons generated by the object. As a result, a signal caused by electrons emitted from the X-ray generator is included in a signal containing information about the object. Accordingly, the S/N ratio is low.

SUMMARY OF THE INVENTION

To solve the above problems, it is an object of the present invention to provide an electron spectroscopic analyzer using X-rays, which is capable of accurately analyzing an object by increasing the X-ray transmission efficiency and increasing a signal to noise (S/N) ratio in an analysis signal containing information about the object at which X-rays are radiated.

To achieve the above object of the invention, there is provided an electron spectroscopic analyzer that includes an X-ray generator for generating X-rays, an optical system for detecting charged particles emitted from an object irradiated with the X-rays to analyze the object, a vacuum system whose inside is maintained at a low pressure near to vacuum pressure, the vacuum system being provided between the X-ray generator and the optical system, and a blocking unit provided between the X-ray generator and the optical system for preventing elements other than the X-rays emitted from the X-ray generator from flowing into the optical system.

Here, the blocking unit is provided within or outside the bellows. The blocking unit may be formed to surround the outside of the bellows. Alternatively, the blocking unit may be provided at the outer bottom of the bellows. The blocking unit may be provided at an inner portion of the vacuum system contacting the X-ray generator or an inner portion of the vacuum system contacting the optical system. The blocking unit provided outside the vacuum system may be a magnet.

The blocking unit provided at an inner portion of the vacuum system contacting the X-ray generator or at an inner portion of the vacuum system contacting the optical system may be a plate formed of a predetermined material which is transparent with respect to X-rays but is opaque with respect to elements other than X-rays emitted from the X-ray generator. The plate has a predetermined thickness. Here, the blocking unit may be selectively formed at only one of the inner portion of the vacuum system contacting the X-ray generator and the inner portion of the vacuum system contacting the optical system.

The blocking unit provided at the inner portion of the vacuum system contacting the optical system may be a plate which is transparent with respect to X-rays and other emitted elements and to which power is applied so that an electric field having the same characteristics as an electric field formed from other emitted elements can be formed within the bellows.

Alternatively, the blocking unit provided at the inner portion of the vacuum system contacting the optical system may have a center which is transparent with respect to X-rays and a shield around the center which is opaque with respect to X-rays. Power is applied to the blocking unit so that an electric field having the same characteristics as an electric field formed from the other emitted elements can be formed within the bellows.

A blocking unit provided at the inner portion of the vacuum system contacting the X-ray generator and/or a blocking unit provided at the inner portion of the vacuum system contacting the optical system may be implemented using a plate or plates thin enough to be transparent with respect to the X-rays and the other emitted elements from the X-ray generator. However, when the two blocking units are combined, a plate opaque with respect to the other emitted elements is formed.

The magnet may be an electromagnet and may be composed of at least two independent electromagnets.

The electron spectroscopic analyzer further includes a collector for collecting elements deflected by the magnet among the emitted elements other than the X-rays, the collector being integrated with the vacuum system between the magnet and the optical system.

Where the blocking unit provided at the inner portion of the vacuum system contacting the X-ray generator or the blocking unit provided at the inner portion of the bellow contacting the optical system is a plate which is transparent with respect to the X-rays and is partially transparent with respect to the emitted elements other than the X-rays, the other blocking unit is the shield.

The electron spectroscopic analyzer further includes a bottleneck portion provided in the middle of the vacuum system for preventing the other emitted elements from flowing into the optical system.

As described above, the present invention is provided with a vacuum system between an X-ray generator and an optical system and a blocking unit within or outside of the bellows. The blocking unit restrains or blocks inflow of elements other than X-rays emitted from the X-ray generator, particularly charged particles, to the optical system. Accordingly, the S/N ratio in a signal measured in the optical system can be increased, thereby increasing the accuracy of an object analysis. In addition, absorptivity of the X-rays can be reduced, thereby increasing the use efficiency of X-rays.

BRIEF DESCRIPTION OF THE DRAWINGS

The above object and advantages of the present invention will become more apparent by describing in detail preferred embodiments thereof with reference to the attached drawings in which.

DETAILED DESCRIPTION OF THE INVENTION

Hereinafter, embodiments of the present invention will be described in detail with reference to the attached drawings. In the drawings, the thicknesses of layers or regions are exaggerated for clarity. Also, the x-rays may be generated and scanned across an object using known technology and an axis of the optical system at the object can be at an angle to the path of the x-rays as in conventional photoelectron spectroscopy devices. However, these specific details of conventional devices will not be shown in order to emphasise the present invention.

First Embodiment

Figure 1:
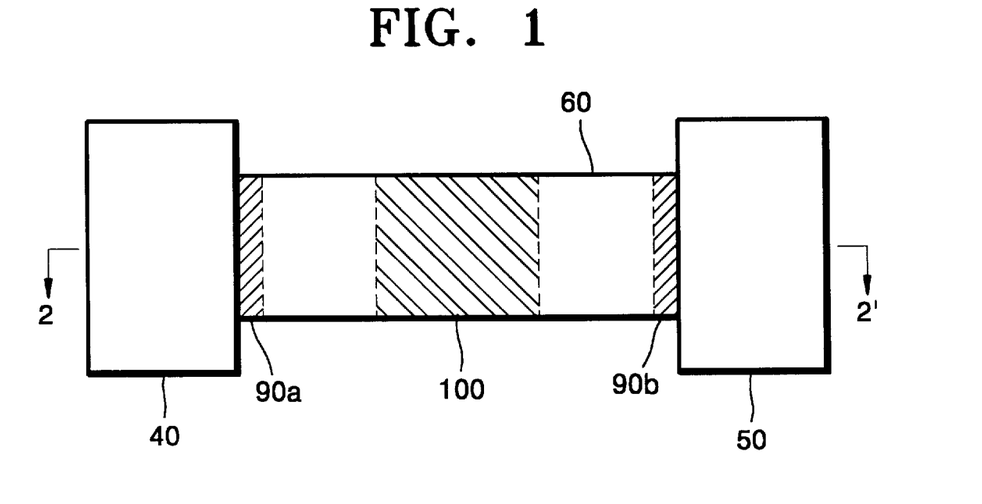
FIG. 1 is a plan view of an electron spectroscopic analyzer using X-rays according to a first embodiment of the present invention.

Referring to FIG. 1, reference numeral 40 denotes an X-ray generator for generating X-rays used for analyzing an object. Reference numeral 50 denotes an optical system facing the X-ray generator 40. The optical system 50 measures a signal corresponding to charged particles, for example, electrons, emitted from an object to be analyzed at which X-rays generated from the X-ray generator 40 are radiated, in order to analyze the object. A vacuum system 60 is provided between the X-ray generator 40 and the optical system 50 to be coupled to both. The vacuum system 60 includes an X-ray inlet (not shown) at its portion contacting the X-ray generator 40 and an X-ray outlet (not shown) at its portion contacting the optical system 50. The internal pressure of the vacuum system 60 is low and near to vacuum pressure (e.g., a pressure of $10^{-5}$ Torr or less) so that the amount of X-ray absorbing gas in the vacuum system 60 is very low. Accordingly, absorption of X-rays, particularly soft X-rays, generated by the X-ray generator 40, while travelling to the optical system 50 can be markedly reduced.

Figure 2:
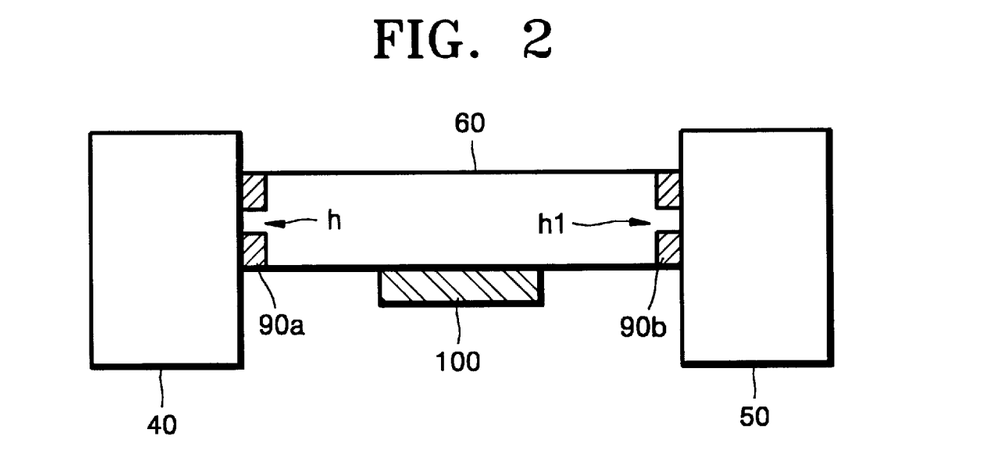
FIG. 2 is a cross-sectional view of the electron spectroscopic analyzer of FIG. 1, taken along the line 2–2N.

A first shield 90a is provided at a portion at which the vacuum system 60 contacts the X-ray generator 40. The first shield 90a is an example of a blocking unit for preventing thermal electrons of high energy, which are used by the X-ray generator 40 for emission of X-rays, from flowing out of the X-ray generator 40. The first shield 90a is formed of a metal having excellent conductivity. Referring to FIG. 2, which is a cross-sectional view taken along the line 2–2' of FIG. 1, a hole "h" is formed in a part of the first shield 90a corresponding to the X-ray inlet of the vacuum system 60. Since thermal electrons in addition to X-rays can be emitted from the X-ray generator 40, it is preferable to form the hole "h" to have a diameter as small as possible in a range in which the X-rays are not blocked. The portion of the first shield 90a other than the hole "h" blocks all or nearly all elements emitted from the X-ray generator 40. A second shield 90b is provided at a portion at which the vacuum system 60 contacts the optical system 50. The second shield 90b is an example of a blocking unit for preventing elements other than X-rays emitted from the X-ray generator 40 from flowing into the optical system 50. In contrast to the first shield 90a, the second shield 90b is formed of an insulating material. A hole "h1" is formed at the center of the second shield 90b to correspond to the hole "h" of the first shield 90a.

Although the object of the present invention can be achieved by using only the first and second shields 90a and 90b, a third blocking unit besides the first and second shields 90a and 90b may be provided between the X-ray generator 40 and the optical system 50 in order to obtain more accurate analysis of an object by increasing an effect of blocking emitted elements other than X-rays, particularly thermal electrons. A magnet 100 provided on the bottom of the vacuum system 60 between the first and second shields 90a and 90b is an example of the third blocking unit. The shape of type of the magnet 100 is not limited as long as the magnet 100 has a magnetic field deflecting charged particles, particularly thermal electrons, moving toward the optical system 50 in the vacuum system 60 away from the X-ray generator 40. The magnet 100 may be a permanent magnet or an electromagnet which satisfies the above condition.

Since it is anticipated that X-rays and other emitted elements passing through the first shield 90a move toward the optical system 50 roughly parallel to the vacuum system 60, it is preferable that the magnetic field is formed to be perpendicular to the vacuum system 60 in order to provoke maximum interaction between the magnetic field and the other emitted elements in the vacuum system 60. As long as the magnetic field can be formed to be perpendicular to the path of elements travelling toward the optical system 50 in the vacuum system 60, e.g., as long as the magnetic field is perpendicular to the vacuum system 60, the magnet 100 can be provided at the side, top, bottom or two opposing sides of the vacuum system 60, for example.

Meanwhile, since the second shield 90b is formed of an insulating material, when an element, particularly a charged particle emitted from the X-ray generator 40 other than X-rays, collides with the second shield 90b, a charge-up phenomenon in which a charge is accumulated at a portion of the second shield 90b with which the charged particle collides occurs. Therefore, in the case where the charged particles are thermal electrons which have been used for generation of an X-rays, a charge of a negative polarity which is the same as the thermal electron is accumulated at the second shield 90b, thereby forming an electric field (hereinafter, referred to as a "negative electric field" for clarity) around the second shield 90b. That is, the second shield 90b is the source of the negative electric field.

As described above, since a negative electric field is formed around the second shield 90b due to the collision of negatively charged particles with the second shield 90b, electrons emitted from the X-ray generator 40 and incident on the optical system 50 are repelled by the negative electric field, which reduces the incidence of electrons.

Second Embodiment

Figure 3:
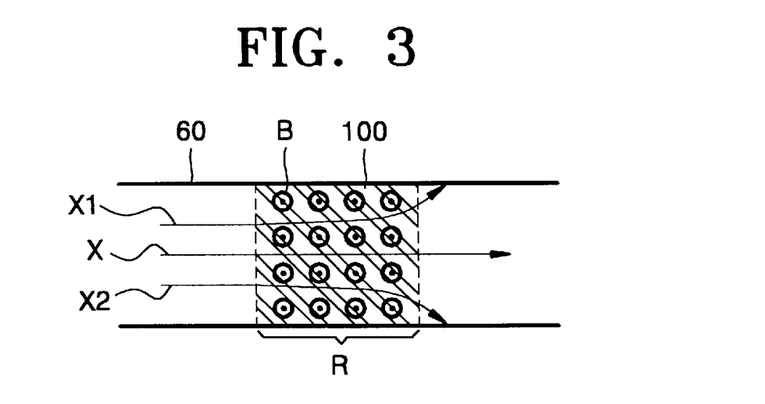
FIG. 3 is a plan view of the interaction between a magnetic field and elements emitted from an X-ray generator of an electron spectroscopic analyzer using X-rays according to a second embodiment of the present invention.

As shown in FIG. 3, when X-rays X and charged elements X1 and X2 emitted parallel to the vacuum system 60 are incident on an upward magnetic field B perpendicular to the vacuum system 60 in the vacuum system 60, the direction of propagation of the X-ray X does not change even after the X-ray X comes out of a magnetic field region R, but the other emitted elements X1 and X2 experience magnetic force in a direction perpendicular to their moving direction in the magnetic field region R and collide with the wall of the vacuum system 60 within or outside the magnetic field region R depending on their momentum and the strength of the magnetic field B. When using a magnetic field as described above, charged particles can be deflected away from the optical system 50, but the wall of the vacuum system 60 may be damaged from bombardment by high-energy charged particles.

Figure 4:
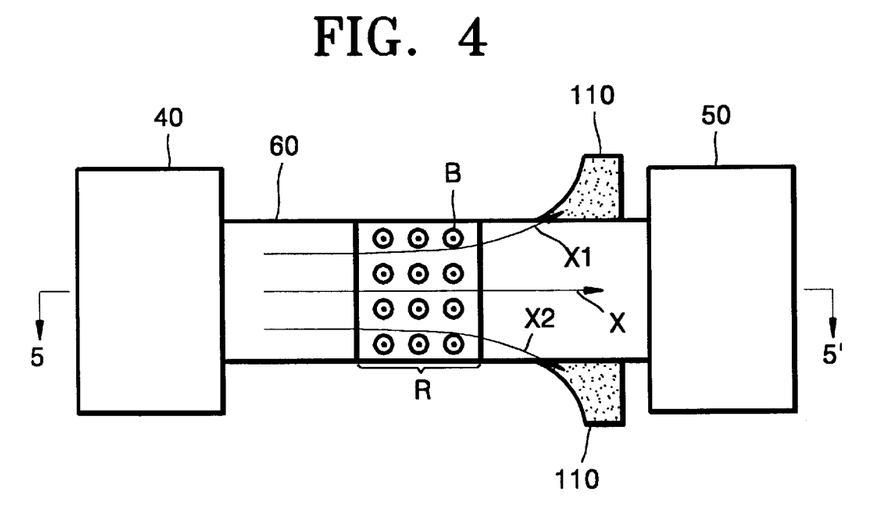
FIG. 4 is a plan view of an electron spectroscopic analyzer using X-rays according to second embodiment of the present invention.
Figure 5:
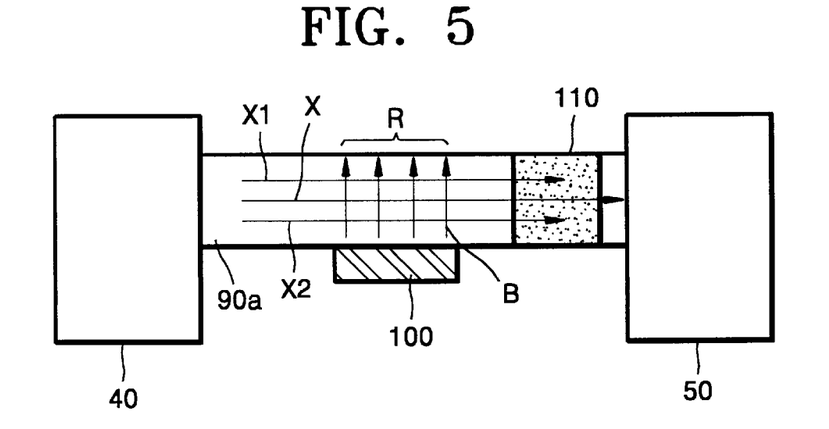
FIG. 5 is a cross-sectional view of the electron spectroscopic analyzer of FIG. 4, taken along the line 5–5N.

To overcome this problem, as shown in FIGS. 4 and 5 (a magnet is not shown in FIG. 4 for convenience), an electron spectroscopic analyzer according a second embodiment of the present invention includes a collector 110 for collecting the other emitted elements X1 and X2 at a portion of the wall of the vacuum system 60 with which the other emitted elements X1 and X2 having passed through the magnetic field region R collide. When other emitted elements X1 and X2 collide with the wall of the vacuum system 60 within the magnetic field region R due to low energy, they can be deflected toward the collector 110 by reducing the strength of the magnetic field B or shortening the length of the magnetic field region R. Here, for the magnet 100, an electromagnet is more preferable than a permanent magnet.

As described above, to change the width of the magnetic field region R according to the energy of the other emitted elements X1 and X2 from the X-ray generator 40, a magnet can be composed of a plurality of independent elements, and the independent elements can be selectively used.

Figure 6:
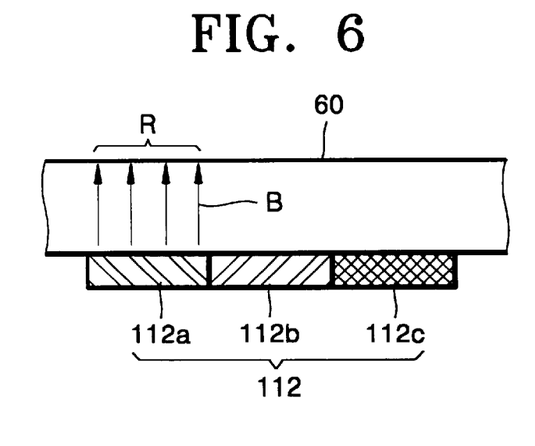
FIG. 6 is a cross-sectional view of the configuration of a magnet provided for an electron spectroscopic analyzer using X-rays according to the second embodiment of the present invention.

For example, as shown in FIG. 6, when a magnet 112 is composed of independent first through third electromagnets 112a, 112b, and 112c, and the first through third electromagnets 112a, 112b, and 112c are selectively used according to the energy of the other emitted elements X1 and X2 from the X-ray generator 40, the magnetic field region R of the magnet 112 can be lengthened or shortened. In other words, when power is applied to all of the first through third electromagnets 112a, 112b, and 112c, the length of the magnetic field region R is maximized. In contrast, when power is applied to only one magnet (for example, the first electromagnet 112a), the length of the magnetic field region R is minimized.

Third Embodiment

Figure 7:
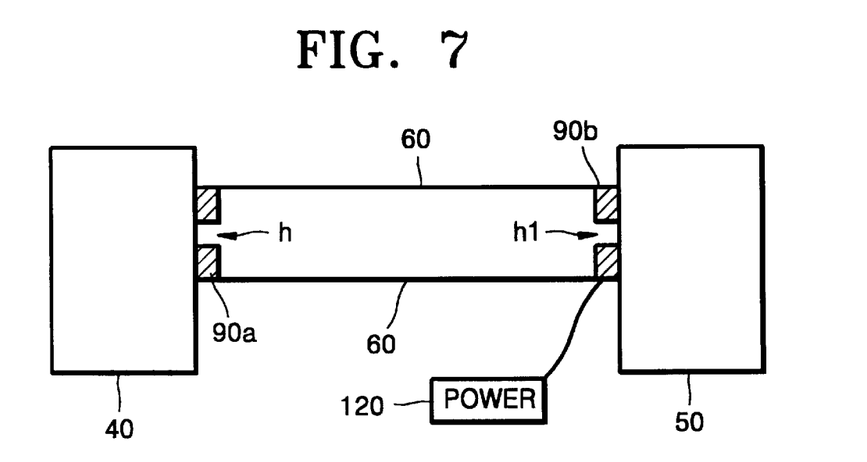
FIGS. 7 through 9 are cross-sectional views of examples of an electron spectroscopic analyzer using X-rays according to a third embodiment of the present invention.

A third embodiment of the present invention is characterized by an electric field artificially formed within a vacuum system 60. Referring to FIG. 7, an electron spectroscopic analyzer is provided with first and second shields 90a and 90b as a blocking unit for preventing charged particles emitted from an X-ray generator 40 from being incident on an optical system 50, within the vacuum system 60. Here, power 120 is applied to the second shield 90b, thereby forming a negative electric field within the vacuum system 60.

As described above, by applying external power to the second shield 90b, not only are the charged particles prevented from flowing into the optical system 50, but also the second shield 90b is protected from damage due to the collision of charged particles.

Figure 8:
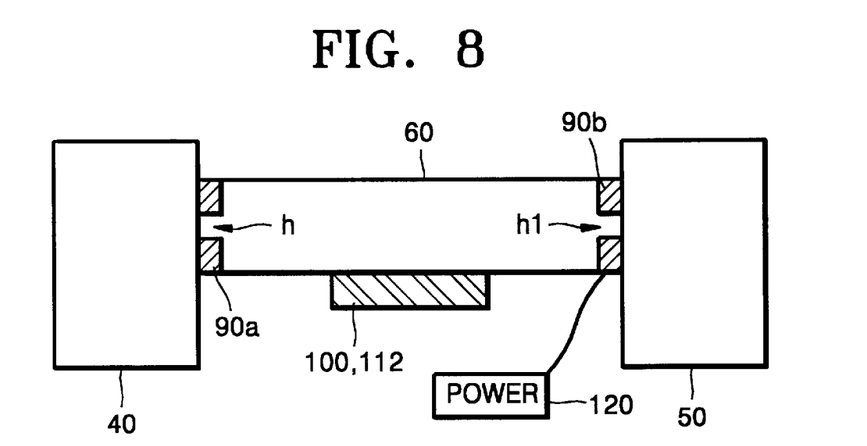

Referring to FIG. 8, an electron spectroscopic analyzer is provided with a blocking unit for preventing charged particles from entering the optional system 50, the blocking unit including first and second shields 90a and 90b within the vacuum system 60 and a magnet 100 or 112 outside the vacuum system 60 for deflecting charged particles away from the optical system 50. Here, power 120 is applied to the second shield 90b.

Figure 9:
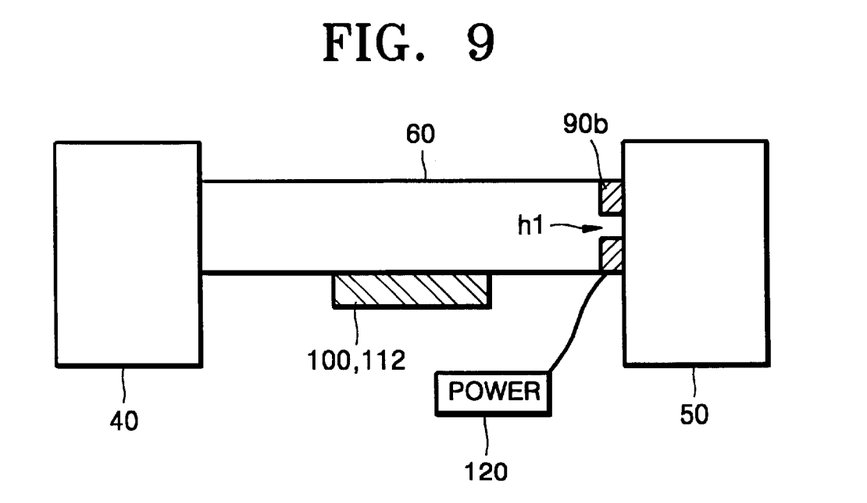

Referring to FIG. 9, an electron spectroscopic analyzer is provided with a blocking unit for preventing charged particles from entering the optional system 50, the blocking unit including a magnet 100 or 112 for deflecting charged particles away from the optical system 50 outside the vacuum system 60 and only a second shield 90b within the vacuum system 60. Here, power 120 is applied to the second shield 90b.

Fourth Embodiment

A fourth embodiment of the present invention uses a difference in transmissivity between an X-ray and other emitted element which are generated by an X-ray generator 40 and is characterized by a transparent plate used as a blocking unit, instead of using the first and second shields 90a and 90b.

Figure 10:
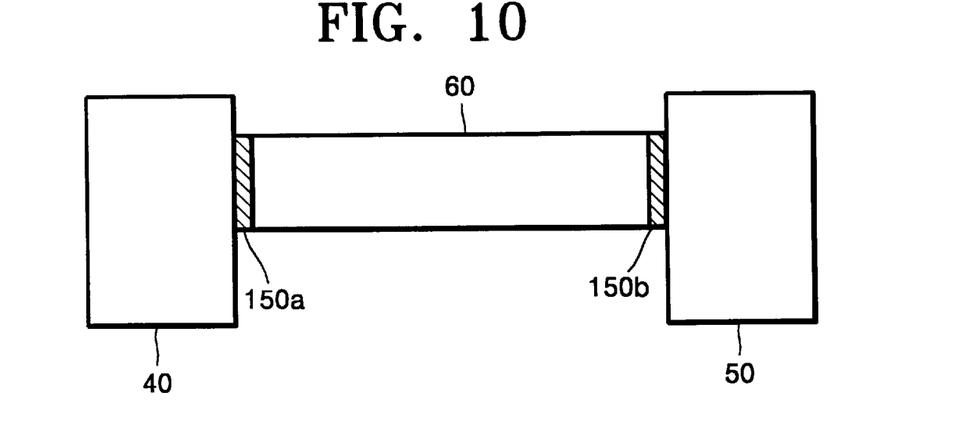
FIGS. 10 through 13 are cross-sectional views of examples of an electron spectroscopic analyzer using X-rays according to a fourth embodiment of the present invention.

Referring to FIG. 10, a first plate 150a is provided at an inner portion of a vacuum system 60 contacting the X-ray generator 40, and a second plate 150b is provided at an inner portion of a vacuum system 60 contacting an optical system 50. One of the first and second plates 150a and 150b is transparent with respect to both X-rays and other elements emitted from the X-ray generator 40. However, when the first and second plates 150a and 150b are combined, they are opaque with respect to the other elements. Accordingly, X-rays pass through the first plate 150a and then can pass through the second plate 150b. However, other emitted elements, and particularly charged particles, consume their energy due to interaction with particles constituting the first plate 150a while passing through the first plate 150a. As a result, the charged particles which have passed through the first plate 150a do not have enough energy to pass through the second plate 150b and thus can be blocked by the second plate 150b even if they pass through the first plate 150a.

Such selective characteristics of the first and second plates 150a and 150b as described above are determined according to the materials and thicknesses of the first and second plates 150a and 150b.

In the case where the first and second plates 150a and 150b are formed of the same material, when the thickness of a plate necessary for blocking charged particles while passing X-rays is $T_{min}$, the preferred thickness of each of the first and second plates 150a and 150b is $T_{min}/2$. However, the thickness of the first plate 150a may be less than $T_{min}/2$ and the thickness of the second plate 150b may be greater than $T_{min}/2$, or vice versa, as long as the combined thickness of the first and second plates 150a and 150b is $T_{min}$.

In the case where the first and second plates 150a and 150b are formed of different materials, for example, the second plate 150b is formed of a material having a density higher than the first plate 150a, it is preferable that the first plate 150a is thicker than the second plate 150b.

Figure 11A:
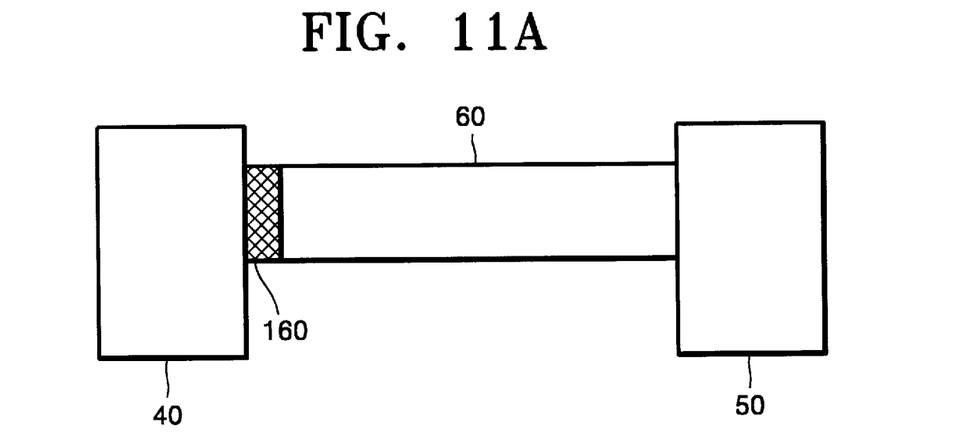
Figure 11B:
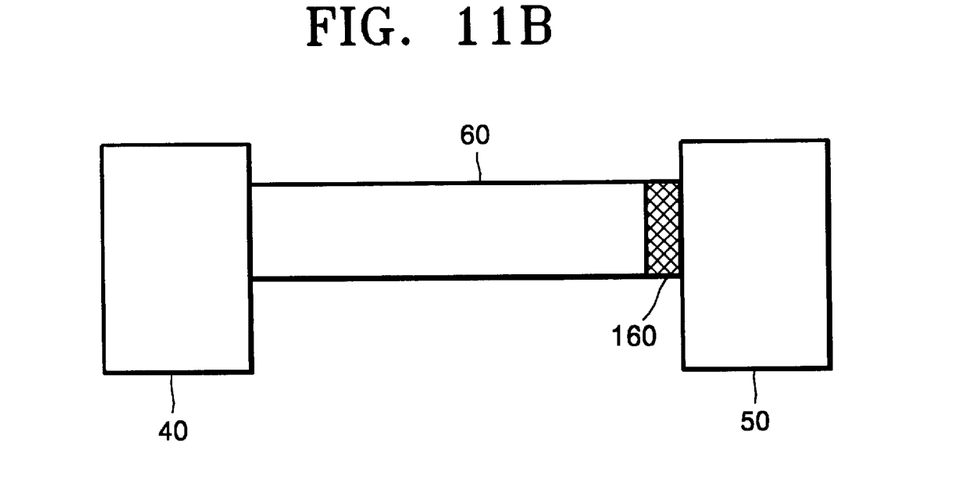

Meanwhile, instead of the first and second plates 150a and 150b, a single plate (referred to as a "third plate" below) having the same thickness as the combined thickness of the first and second plates 150a and 150b can be used. Such an example is shown in FIGS. 11A and 11B. Referring to FIGS. 11A and 11B, a third plate 160 is provided at an inner portion of a vacuum system 60 contacting an X-ray generator 40, as shown in FIG. 11A, or at an inner portion of the vacuum system 60 contacting an optical system 50, as shown in FIG. 11B.

Figure 12:
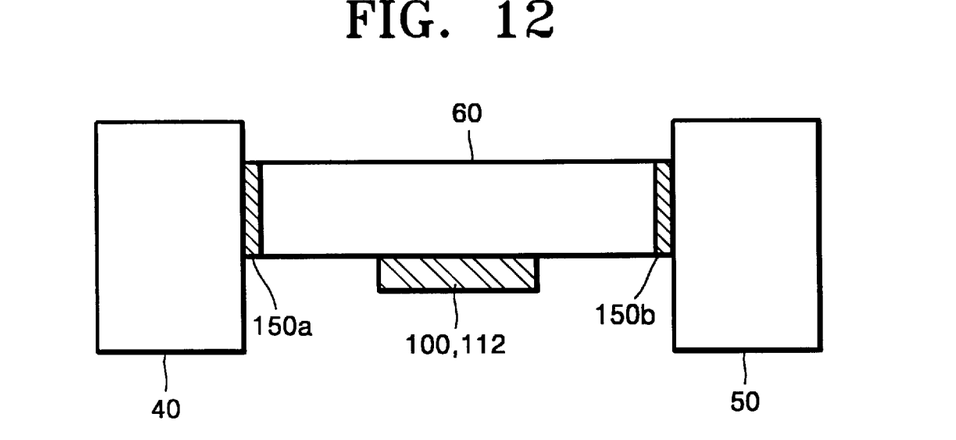

Referring to FIG. 12, a magnet 100 or 112 deflecting charged particles passing through a first plate 150a away from an optical system 50 is provided outside a vacuum system 60 between the first and second plates 150a and 150b.

Figure 13:
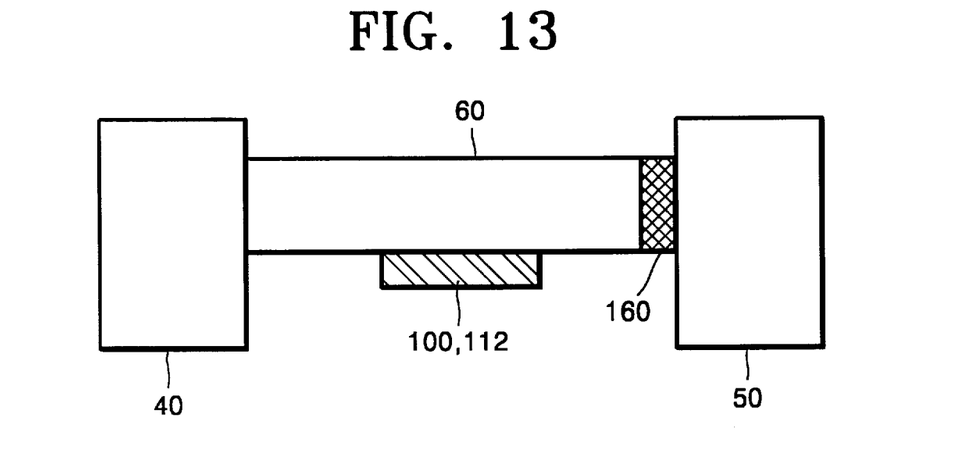

In addition, referring to FIG. 13, a magnet 100 or 112 deflecting charged particles is provided outside a vacuum system 60, and a third plate 160 is provided at an inner portion of the vacuum system contacting the optical system 50.

As described above, by using the first and second plates 150a and 150b together or the third plate 160 and the magnet 100 or 112 together, charged particles are more effectively prevented from entering into the optical system 50.

Fifth Embodiment

Figure 14:
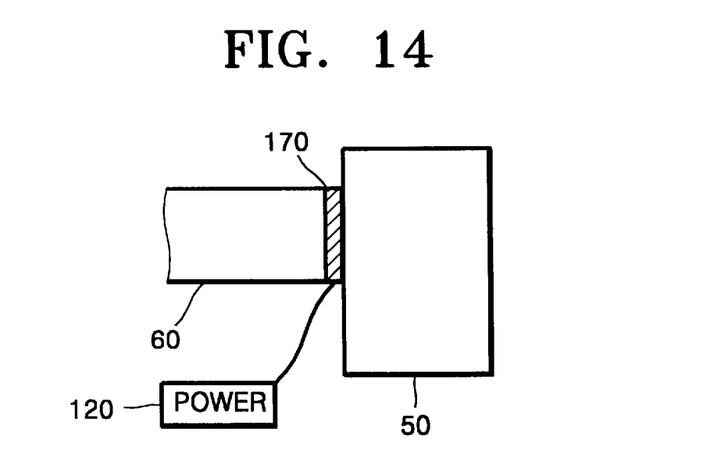
FIG. 14 is a cross-sectional view of an electron spectroscopic analyzer using X-rays according to a fifth embodiment of the present invention.

As shown in FIG. 14, a fifth embodiment of the present invention is characterized by an electric field formed within a vacuum system 60 by applying power 120 to a plate 170. Here, the plate 170 is one selected from the second plate 150b and the third plate 160 shown in the fourth embodiment. A first plate 150a or a first shield 90a may also be provided at a portion of the vacuum system 60 which is not shown in FIG. 14. A magnet may be further provided for deflecting charged particles.

Sixth Embodiment

An electron spectroscopic analyzer according to a sixth embodiment includes one of the first and second shields 90a and 90b and one of the first and second plates 150a and 150b and may selectively include a magnet.

Figure 15:
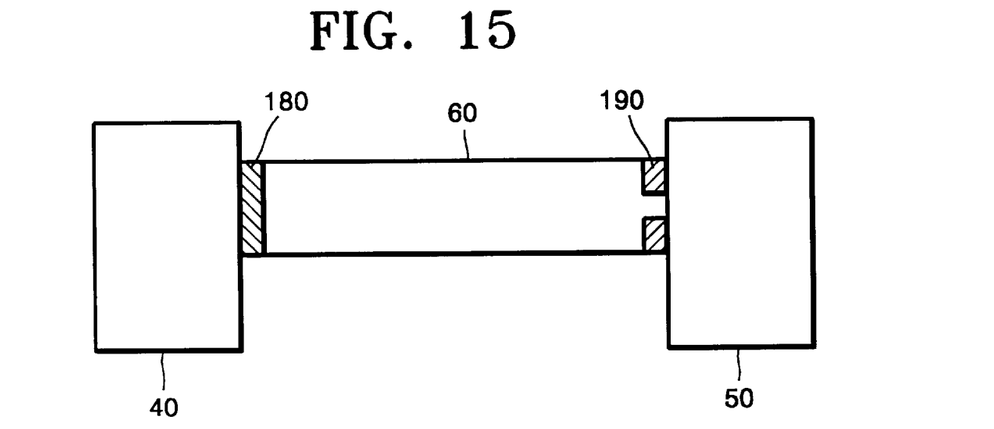
FIGS. 15 through 17 are cross-sectional views and a plan view of examples of an electron spectroscopic analyzer using X-rays according to a sixth embodiment of the present invention.

More specifically, referring to FIG. 15, a plate 180 is provided in an inner portion of a vacuum system 60 contacting an X-ray generator 40. The plate 180 is transparent with respect to X-rays emitted from the X-ray generator 40 but is partially transparent or opaque with respect to other elements, particularly charged particles, emitted from the X-ray generator 40. The plate 180 is realized as one of the first and second plates 150a and 150b described in the fourth embodiment. A shield 190 is provided in an inner portion of the vacuum system 60 contacting an optical system 50. The shield 190 is provided for preventing charged particles which have passed through the plate 180 from being incident on the optical system 50. The shield 190 is realized as the second shield 90b described in the first embodiment.

Figure 16:
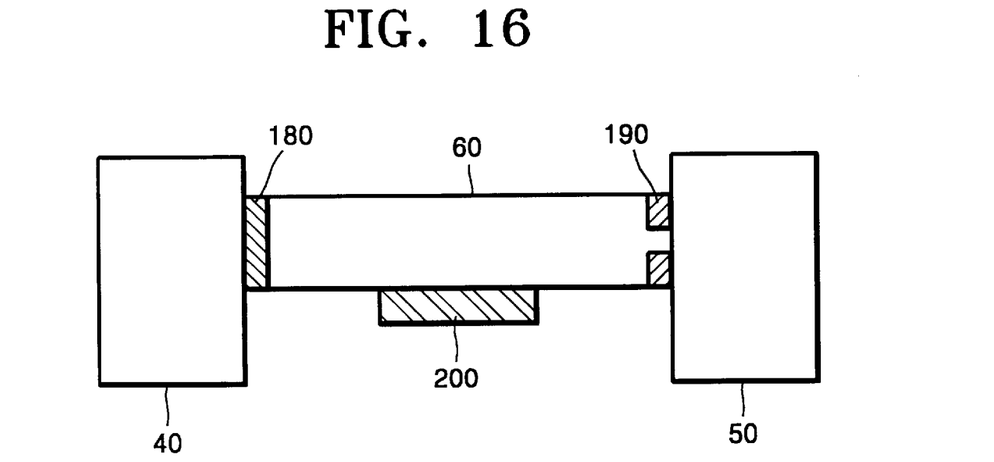

Referring to FIG. 16, a magnet 200 for deflecting charged particles which have passed through a plate 180 is provided outside a vacuum system 60 between the plate 180 and a shield 190. For the magnet 200, a permanent magnet may be used but an electromagnet is preferable.

Figure 17:
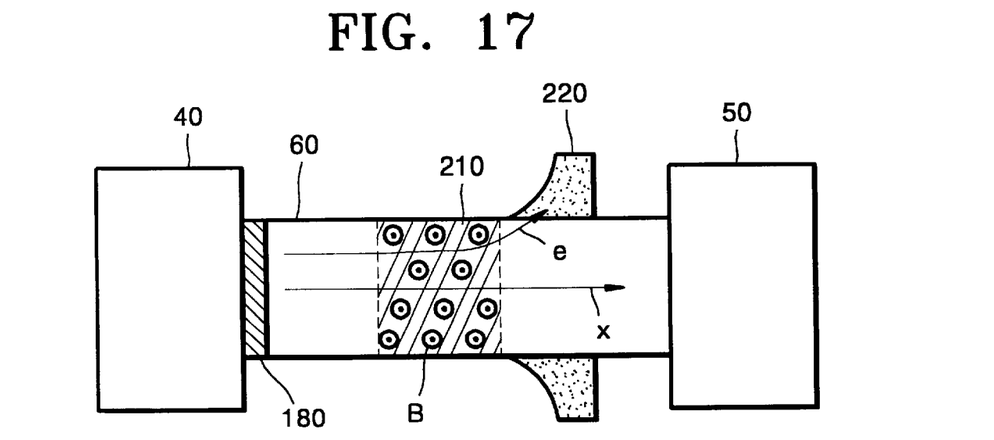

Referring to FIG. 17, a plate 180 is provided in an inner portion of a vacuum system 60 contacting an X-ray generator 40, and a magnet 210 for forming a magnetic field across the vacuum system 60 is provided outside the vacuum system 60 between the plate 180 and an optical system 50. In addition, a collector 220 for collecting charged particles deflected by the magnet 210 is provided between the magnet 210 and the optical system 50. The collector 220 is integrated with the vacuum system 60. Here, reference character B denotes an upward magnetic field formed due to the magnet 210. Reference characters X and e denote an X-ray and an electron, respectively, which are emitted from the X-ray generator 40. Since the X-ray X does not have a charge, it is directly incident on the optical system 50 without being influenced by the magnetic field B. In contrast, the electron e is deflected toward the collector 220 due to interaction with the magnetic field B.

Meanwhile, like the embodiment shown in FIG. 3, an electric field can be formed within the vacuum system 60 by applying power to the shield 190 of the electron spectroscopic analyzers shown in FIGS. 15 and 16, thereby increasing an effect of blocking charged particles emitted from the X-ray generator 40.

Test Example

Copper (Cu) was analyzed using a conventional electron spectroscopic analyzer including an X-ray generator having power of 1.5 kW (30 kV and 50 mA), and using an electron spectroscopic analyzer according to the first embodiment of the present invention including an X-ray generator having power of 7.5 kW (30 kV and 250 mA).

Figure 18:
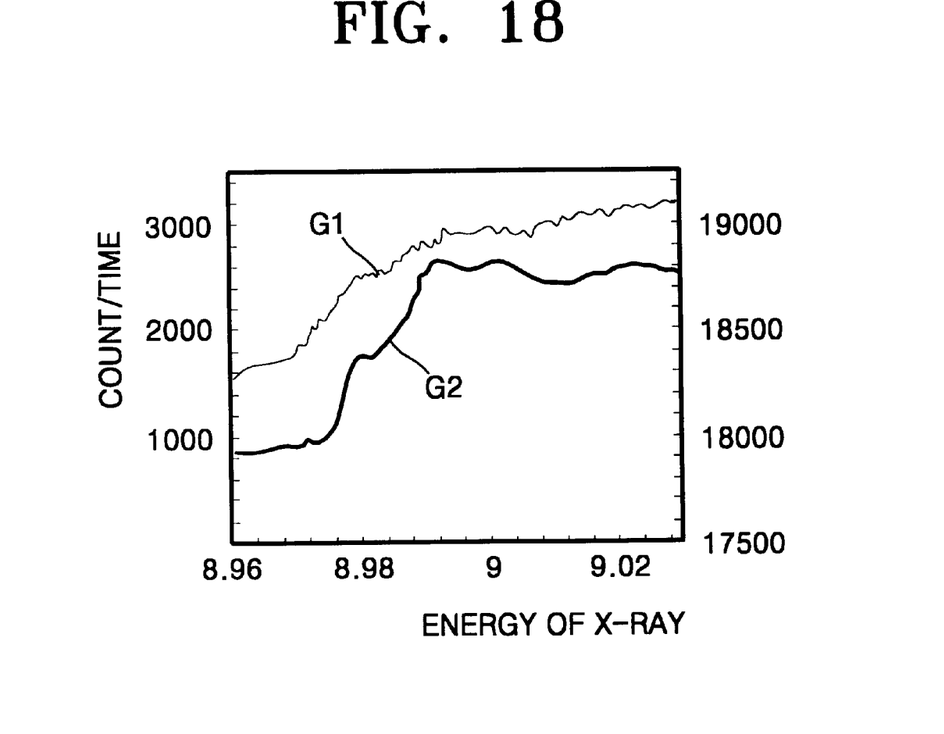
FIG. 18 is a graph of the results of tests carried out for comparing the performance of an electron spectroscopic analyzer using X-rays according to the present invention with the performance of an electron spectroscopic analyzer using X-rays according to prior art.

In FIG. 18, a first graph G1 denotes the result when the conventional electron spectroscopic analyzer was used, and a second graph G2 denotes the result when the electron spectroscopic analyzer according to the first embodiment of the present invention was used. In FIG. 18, the horizontal axis denotes the energy of X-rays radiated at the object to be analyzed, and both vertical axes denote the count per unit time of electrons emitted from the object to be analyzed in response to irradiation by the X-rays. The vertical axis on the left applies to the second graph G2, and the vertical axis on the right applies to the first graph G1.

Referring to the first and second graphs G1 and G2, the measured rate of electron emission from the copper in an optical system according to conventional technology was much greater than that in the present invention, even when the power of the X-ray generator of the conventional electron spectroscopic analyzer was as small as ⅕ of the power of the electron spectroscopic analyzer according to the present invention. This is because only electrons emitted from the copper are detected by the electron spectroscopic analyzer of the present invention while both electrons emitted from the copper and electrons emitted from the X-ray generator which are incident on the optical system are detected by the conventional electron spectroscopic analyzer.

Copper has a K absorption edge of 8.981 KeV. Accordingly, when 8.981 KeV X-rays are radiated at copper, they are readily absorbed, and emission of roughly 8.981

KeV electrons increases, thereby greatly increasing the number of electrons measured by an optical system per unit time. Consequently, it is anticipated that an increases in electron emission will appear on a graph when the energy of the radiated X-rays becomes 8.981 KeV.

However, the 8.981 KeV absorption edge of copper does not appear in the first graph G1. In contrast, in the second graph G2, when the energy value of a radiated X-ray becomes 8.981 KeV, the absorption edge is quite visible.

Such a sign does not appear in the first graph G1 because electrons emitted from copper are mixed with electrons of high energy continuously emitted from an X-ray generator and incident on an optical system when the energy of the X-rays becomes 8.98 KeV. Accordingly, it is difficult to discriminate a signal corresponding to electrons emitted from the copper from an entire measured signal.

Figure 19:
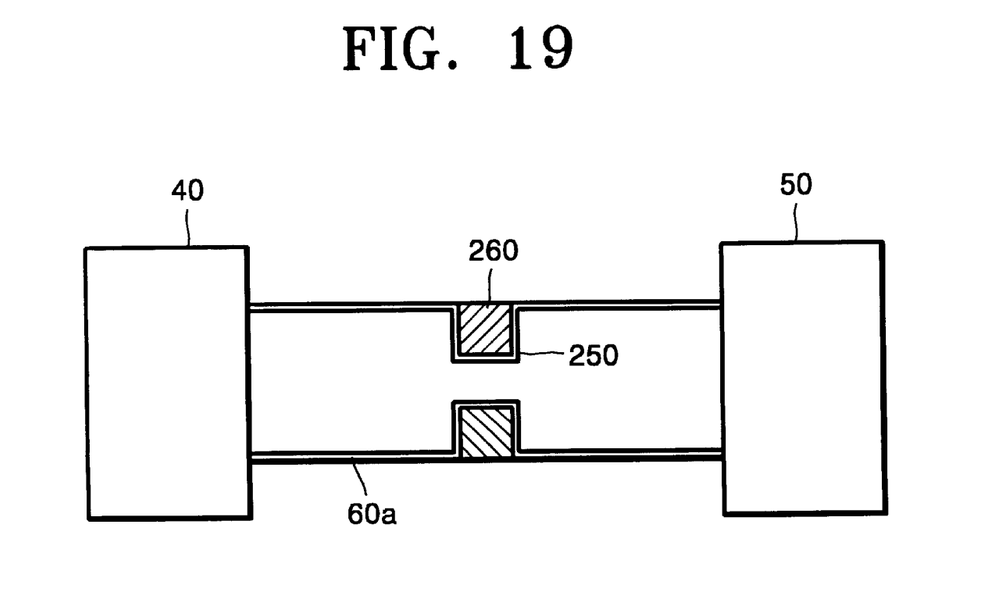
FIG. 19 is a cross-sectional view of an electron spectroscopic analyzer using X-rays according to another embodiment of the present invention.

While this invention has been particularly shown and described with reference to preferred embodiments thereof, it should not be construed as being limited to these embodiments. These embodiments should be understood as examples. For example, it will be understood by those skilled in the art that a member having the same function as a vacuum system but having a different form than the vacuum system can be formed between an X-ray generator and an optical system. For example, as shown in FIG. 19, it can be considered that an electron spectroscopic analyser is provided with a bottleneck portion 250 in the middle of a vacuum system 60a and a magnet 260 around the bottleneck portion 250. A permanent magnet can be used for the magnet 260, but it is preferable to use an electromagnet. Elements other than X-rays emitted from an X-ray generator 40 can be blocked by the bottleneck portion 250. Even if the other emitted elements, for example, electrons, pass through the bottleneck portion 250, the other emitted elements are deflected away from an optical system 50 due to a magnetic field formed across the bottleneck portion 250 by the magnet 260.

Meanwhile, since the bottleneck portion 250 may be heated due to bombardment by charged particles emitted from the X-ray generator 40, a cooling unit may be provided between the magnet 260 and the bottleneck portion 250 to cool down the heated bottleneck portion 250. Numerous variations of electron spectroscopic analyzers obtained by combining electron spectroscopic analyzers according to the first through sixth embodiments may be implemented.

As described above, the present invention is provided with a vacuum bellows, the inside of which is maintained at a low pressure near to vacuum pressure, between an X-ray generator and an optical system. Accordingly, absorption of X-rays by gas within the vacuum system can be reduced, thereby increasing the X-ray transmission efficiency. In addition, a unit for restricting or blocking inflow of elements other than X-rays emitted from the X-ray generator, particularly charged particles, into the optical system is provided within or outside the bellows. Therefore, the S/N ratio of a signal measured in the optical system of an electron spectroscopic analyzer is increased, thereby increasing the accuracy and precision of X-ray absorption analysis.

What is claimed is:

1. An electron spectroscopic analyzer using X-rays comprising:
    an X-ray generator for generating X-rays;
    an optical system for detecting charged particles emitted from an object irradiated with the X-rays to analyze the object;
    a vacuum system provided between the X-ray generator and the optical system; and
    blocking means provided between the X-ray generator and the optical system for preventing charged particles emitted from the X-ray generator from flowing into the optical system.

2. The electron spectroscopic analyzer of claim 1, wherein the blocking means is provided outside a vacuum system.

3. The electron spectroscopic analyzer of claim 2, wherein the blocking means is a magnet provided at the outer surface of the vacuum system.

4. The electron spectroscopic analyzer of claim 1, wherein the blocking means is provided within a vacuum system.

5. The electron spectroscopic analyzer of claim 1, wherein the blocking means includes at least one of a first blocking means at an inner portion of the vacuum system contacting the X-ray generator and a second blocking means at an inner portion of the vacuum system contacting the optical system, wherein each of said first and said second blocking means for preventing elements other than the X-rays emitted from the X-ray generator from flowing into the optical system.

6. The electron spectroscopic analyzer of claim 5, wherein at least one of the first blocking means provided at the inner portion of the vacuum system contacting the X-ray generator and the second blocking means provided at the inner portion of the vacuum system contacting the optical system is a plate which is transparent with respect to the X-rays but is opaque with respect to the emitted elements other than the X-rays.

7. The electron spectroscopic analyzer of claim 6, further comprising a power supply connected to the plate, wherein said plate is located at the inner portion of the vacuum system contacting the optical system so that an electric field can be formed.

8. The electron spectroscopic analyzer of claim 5, wherein the second blocking means provided at the inner portion of the vacuum system contacting the optical system includes a shield with a hole at the center thereof and which is opaque with respect to the X-rays and the other emitted elements.

9. The electron spectroscopic analyzer of claim 8, further comprising a power supply connected to the shield so that an electric field can be formed.

10. The electron spectroscopic analyzer of claim 5, wherein the second blocking means provided at the inner portion of the vacuum system contacting the optical system is a plate which is transparent with respect to the X-rays and is opaque with respect to the other elements emitted from the X-ray generator.

11. The electron spectroscopic analyzer of claim 5, wherein one of the first blocking means provided at the inner portion of the vacuum system contacting the X-ray generator and the second blocking means provided at the inner portion of a bellows contacting the optical system is a plate which is transparent with respect to the X-rays and is partially transparent with respect to the emitted elements other than the X-rays, and the other of the first and second blocking means is the shield.

12. The electron spectroscopic analyzer of claim 1, wherein the blocking means includes a compound electromagnet composed of at least two independent electromagnets.

13. The electron spectroscopic analyzer of claim 1, further comprising a collector for collecting elements deflected by the blocking means, the collector being integrated with the vacuum system between blocking means and the optical system.

14. The electron spectroscopic analyzer of claim 1, further comprising a bottleneck portion provided in the middle of the vacuum system for preventing the emitted elements other than X-rays from flowing into the optical system.

15. A method of performing electron spectroscopic analysis using X-rays, comprising the steps of:
   generating X-rays in an X-ray generator in a direction to impinge on an object;
   detecting charged particles emitted from the object irradiated with the X-rays from the X-ray generator to analyze the object; and
   preventing charged particles emitted from the X-ray generator from flowing into the optical system.

16. The method of claim 15, wherein the preventing step includes providing an electric field having lines of force in a direction other than the direction of the X-rays from the X-ray source, the electric field deflecting elements other than the X-rays from flowing into the optical system.

17. The method of claim 15, wherein the preventing step includes providing a shield between the X-ray generator and the object.

18. The method of claim 15, wherein the preventing step includes providing a plate between the X-ray generator and the object.

19. The method of claim 15, wherein the preventing step includes providing a charged plate between the X-ray generator and the object.

* * * * *